(12) United States Patent
Benbijja et al.

(10) Patent No.: US 10,438,128 B2
(45) Date of Patent: Oct. 8, 2019

(54) TREATMENT OF AUTOIMMUNE AND INFLAMMATORY DISEASES WITH THE ARSENIC COMPOUNDS AS2O3 AND/OR AS2O5 ADMINISTERED LOCALLY

(71) Applicants: CENTRE NATIONAL DE LA RECHERCHE SCIENTIFIQUE (CNRS), Paris (FR); UNIVERSITE PARIS-SUD 11, Orsay (FR)

(72) Inventors: Mohcine Benbijja, Paris (FR); Pedro Bobe, Paris (FR)

(73) Assignees: CENTRE NATIONAL DE LA RECHERCHE SCIENTIFIQUE (CNRS), Paris (FR); UNIVERSITE PARIS-SUD 11, Orsay (FR)

( * ) Notice: Subject to any disclaimer, the term of this patent is extended or adjusted under 35 U.S.C. 154(b) by 786 days.

(21) Appl. No.: 14/787,002

(22) PCT Filed: Apr. 25, 2014

(86) PCT No.: PCT/EP2014/058420
§ 371 (c)(1),
(2) Date: Oct. 26, 2015

(87) PCT Pub. No.: WO2014/174059
PCT Pub. Date: Oct. 30, 2014

(65) Prior Publication Data
US 2018/0189671 A1  Jul. 5, 2018

(30) Foreign Application Priority Data
Apr. 26, 2013  (FR) .................................... 13 53870

(51) Int. Cl.
| | | |
|---|---|---|
| *A61K 33/36* | (2006.01) | |
| *G06N 10/00* | (2019.01) | |
| *H01L 23/00* | (2006.01) | |
| *H01L 23/66* | (2006.01) | |
| *A61P 17/06* | (2006.01) | |
| *A61P 17/00* | (2006.01) | |
| *H01L 21/56* | (2006.01) | |

(52) U.S. Cl.
CPC ............ *G06N 10/00* (2019.01); *A61K 33/36* (2013.01); *A61P 17/00* (2018.01); *A61P 17/06* (2018.01); *H01L 23/564* (2013.01); *H01L 23/66* (2013.01); *H01L 24/80* (2013.01); *H01L 21/568* (2013.01); *H01L 2224/0231* (2013.01)

(58) Field of Classification Search
CPC ..... G06N 99/002; H01L 23/564; H01L 23/66; H01L 24/80; H01L 21/568; H01L 2224/0231; A61K 33/36; A61P 29/00; A61P 37/00
USPC .......................................... 257/664; 424/623
See application file for complete search history.

(56) References Cited

U.S. PATENT DOCUMENTS

| | | | | |
|---|---|---|---|---|
| 6,333,028 B1 * | 12/2001 | Berd | .................. | A61K 39/0011 424/193.1 |
| 6,733,792 B1 * | 5/2004 | Lu | ........................ | A61K 9/4875 424/620 |
| 2002/0183385 A1 * | 12/2002 | Ellison | ................. | A61K 31/568 514/504 |
| 2004/0022869 A1 * | 2/2004 | Chen | .................... | A61K 31/337 424/623 |
| 2005/0196464 A1 | 9/2005 | Hu | | |
| 2009/0098216 A1 * | 4/2009 | Chelbi Alix | ........... | A61K 33/36 424/623 |

(Continued)

FOREIGN PATENT DOCUMENTS

| | | | | |
|---|---|---|---|---|
| CA | 1107514 A1 | 8/1981 | | |
| EP | 1736161 A2 * | 12/2006 | ............. | A61K 33/36 |

(Continued)

OTHER PUBLICATIONS

Databacsae [Online] Cheim C Ala Bstracstesr Vicec, Olumbus, Ohio, US; Jun. 21, 2005 (Jun. 21, 2005), Dai Zhaoyu"Na:p plication of arsenic compounds in medicines for treating skin disease", retrieved from STN Database accession No. 2005:533176 abstract & CN1 528 344 A (Dai Zhaoyun [CN]) Sep. 15, 2004 (Sep. 15, 2004).

Tse Wai-Pui et al: "Arsenic trioxide, arsenic pentoxide, and arsenic iodide inhibit humankeratinocyte proliferation through the induction of apoptosis.", The Journal of Pharmacology and Experimental Therapeutics Aug. 2008, vol. 326, No. 2, Aug. 2008 (Aug. 2008), pp. 388-394.

Tse Wai-Pui et al: "Realgar-mediated growth inhibition on HaCaT human keratinocytes is associated with induction of apoptosis.", International Journal of Molecular Medicine Aug. 2009, vol. 24, No. 2, Aug. 2009 (Aug. 2009), pp. 189-196.

LiuZuo et al.: "The research progress of realgar", Mar. 29, 2009 (Mar. 29, 2009), Retrieved from the Internet: URL:http://www.yourpaper.net/article/20090329/83374.html#.U5qt71Psx8E [retrieved on Jun. 13, 2014].

(Continued)

*Primary Examiner* — Nannette Holloman
(74) *Attorney, Agent, or Firm* — Arrigo, Lee, Guttman & Mouta-Bellum LLP (57) ABSTRACT

The invention concerns the field of human auto-immune and/or inflammatory diseases, and more specifically the use of arsenic compounds for the preparation of drugs intended for the treatment and/or prevention of skin injuries associated with auto-immune and/or inflammatory diseases in a human subject. The invention concerns an arsenic compound $As_2O_5$ for use in the treatment and/or prevention of skin injuries associated with auto-immune and/or inflammatory diseases in a human subject, a pharmaceutical composition comprising an arsenic compound $As_2O_5$, preferably for the treatment and/or prevention of skin injuries associated with auto-immune diseases in a human subject, and products containing an arsenic compound $As_2O_5$ and an arsenic compound $As_2O_3$ as a combination product for simultaneous, separated or time-spread use in the treatment and/or prevention of skin injuries associated with auto-immune diseases in a human subject.

15 Claims, 7 Drawing Sheets

(56) References Cited

U.S. PATENT DOCUMENTS

2009/0297624 A1* 12/2009 Alix .................. A61K 33/36
424/623

FOREIGN PATENT DOCUMENTS

| EP | 1736161 A2 | 12/2006 |
|---|---|---|
| WO | 03/090766 A1 | 11/2003 |
| WO | 2008/09782 A2 | 8/2008 |

OTHER PUBLICATIONS

Adachi S et al: "Gel Filtration Profile of the Arsenic Compounds in Water Extracts of Seaweeds", Journal of the Food Hygienic Society of Japan, vol. 21, No. 1, 1980, pp. 13-17.
Database CA [Online] Chemical Abstracts Service Columbus, Ohio, US; Apr. 30, 2007 (Apr. 30, 2007), Liu, Jiayou: "Composition of traditional Chinese medicine lotion for treating psoriasis", retrieved from STN Database accession No. 2007:467634 abstract & CN1 951 440 A (Liu Jiayou [CN]) Apr. 25, 2007 (Apr. 25, 2007).

\* cited by examiner

A) Topical treatment

B) Systemic treatment

TREATMENT OF AUTOIMMUNE AND INFLAMMATORY DISEASES WITH THE ARSENIC COMPOUNDS AS2O3 AND/OR AS2O5 ADMINISTERED LOCALLY

The invention relates to the field of human autoimmune and/or inflammatory diseases, more specifically the use of arsenic compounds in the preparation of medicinal products intended to treat and/or prevent skin lesions associated with essentially autoimmune or inflammatory diseases or with autoimmune diseases having a strong inflammatory component responsible for their initiation and for certain tissue lesions.

Autoimmune diseases are a heterogeneous group of immune system diseases characterized by production by the subject of antibodies directed against the self (also called autoantibodies), i.e., reacting with the subject's own antigens. Some of these diseases have at times been classified as inflammatory diseases, to the extent that they also involve so-called dysimmune mechanisms.

The most common autoimmune and/or inflammatory diseases are: systemic lupus erythematosus, acute disseminated lupus erythematosus, uveitis, Behçet's disease, sarcoidosis, Sjögren's syndrome, rheumatoid polyarthritis, juvenile polyarthritis, Fiessinger-Leroy-Reiter syndrome, gout, osteoarthritis, polymyositis, myocarditis, primary biliary cirrhosis, Crohn's disease, ulcerative colitis, multiple sclerosis and other demyelinating diseases, aplastic anemia, idiopathic thrombocytopenic purpura, any disease associated with non-tumor lymphoproliferation, B-cell lymphoma, Simmonds' panhypopituitarism, Basedow-Graves' disease and Graves' ophthalmopathy, subacute thyroiditis and Hashimoto's disease, Addison's disease, chronic hepatitis, insulin—dependent diabetes mellitus (type 1).

A large number of these pathologies are characterized by dermatological affections, in particular cutaneous or mucocutaneous affections. That is the case in particular of lupus erythematosus, scleroderma, psoriasis, cutaneous vasculitis, vascular purpura, autoimmune bullous dermatoses (bullous pemphigoid, cicatricial pemphigoid, linear IgA dermatosis, dermatitis herpetiformis, epidermolysis bullosa acquisita, pemphigus and variants thereof), dermatitis (atopic, seborrheic, stasis), dermatomyositis, erythema nodosum, pyoderma gangrenosum, eczema (atopic, contact, dyshidrotic), lichen planus, lichen sclerosus et atrophicus, alopecia areata.

Lupus erythematosus in particular is a chronic systemic autoimmune disease, of the family of connective tissue diseases, which is expressed differently depending on the patient. This pathology was the subject of much research, and is often used as a case study for all human autoimmune and/or inflammatory diseases presenting the skin lesions mentioned above.

In lupus erythematosus, there is a distinction between cutaneous lupus erythematosus (CLE) and disseminated lupus erythematosus (DLE) or systemic lupus erythematosus (SLE). CLE is a particularly polymorphic affection traditionally divided into three groups: chronic CLE, which includes discoid lupus, tumid lupus, lupus pernio and lupus profundus (or panniculitis); subacute CLE (SCLE) and acute CLE (ACLE).

Many dermatological manifestations are also observed during SLE. They can be classified schematically into three groups: lupus lesions (histology suggestive of lupus), vascular lesions (cutaneous vasculitis) and other manifestations. The anatomopathological examination of a cutaneous lupus lesion reveals epidermal and dermal lesions: hyperkeratosis, skin atrophy, degeneration of basal keratinocytes, thickening of the basal membrane, edema and dermal infiltrate composed essentially of lymphocytes.

The care of SLE necessitates a basic treatment, generally based on systemic hydroxychloroquine, chloroquine or corticoids. (List of procedures and services ALD 21—"Systemic lupus erythematosus," HAS January 2012). In the case of discoid lupus erythematosus and subacute cutaneous lupus erythematosus, the first-line therapy is based on local application of immunosuppressants commonly used in dermatology, such as corticoids or tacrolimus. When local treatments fail, systemic treatments based on hydroxychloroquine and/or chloroquine, or thalidomide (even methotrexate in the severe forms of the disease, in particular with the objective of limiting the use of cortisone), are administered.

When they exist, treatments for human autoimmune and/or inflammatory diseases presenting skin lesions other than lupus cited above, in particular scleroderma, psoriasis, cutaneous vasculitis, vascular purpura, autoimmune bullous dermatoses (in particular bullous pemphigoid, cicatricial pemphigoid, linear IgA dermatosis, dermatitis herpetiformis, epidermolysis bullosa acquisita, pemphigus and variants thereof), dermatitis, (in particular atopic dermatitis, seborrheic dermatitis, stasis dermatitis), dermatomyositis, erythema nodosum, pyoderma gangrenosum, eczema (in particular atopic eczema, contact eczema, dyshidrotic eczema), lichen planus, lichen sclerosus et atrophicus, and alopecia areata.

However, these treatments have well-known disadvantages. Generally, immunosuppressants, by decreasing immune responses nonspecifically, expose the body to complications from viral or bacterial infection and, later, to the development of malignant diseases.

Furthermore, the ocular toxicity of chloroquine and hydroxychloroquine, leading principally to corneal damage and retinopathy, has long been described. The retinopathy is sometimes irreversible, and may result in a significant loss of vision.

The side effects of the administration of corticoids, in systemic application and in local application, are also well known. In particular, the topical administration of corticoid is associated with higher risks of infection and with skin atrophy, as well as with the phenomena of tachyphylaxis and the rebound effect. The practical effect of tachyphylaxis is the appearance of tolerance, and in the long term of resistance, of the dermatosis to treatment after extended, uninterrupted applications. The rebound effect is the fresh outbreak of dermatosis following sudden termination of topical corticosteroids, after extended treatment.

The undesirable effects of Tacrolimus observed consist above all of a burning sensation, itching or erythema at the site of application, while the long-term undesirable effects are still poorly known. As for Methotrexate, the extent of its undesired effects, namely a decrease in white blood cells, digestive problems (nausea, pain, vomiting, ulcers), damage to the lungs and liver, infections and hair loss, explains why its use remains exceptional.

The use of arsenic compounds systemically to treat autoimmune pathologies has been disclosed (EP 1 499 330). These systemic treatments enable skin lesions associated with lupus to be resorbed. However, this systemic use has the disadvantage of being general and nonspecific. Local application of arsenic compounds appears contraindicated in the case of skin lesions, whereas it is known that these compounds, and in particular $As_2O_3$, are irritant products, causing in case of contact with the skin a reddening, and even burns. Extended and repeated contact with dilute $As_2O_3$ solutions is known to irritate the skin and cause dermatitis.

There is thus a need for compounds for alternative treatments of autoimmune and/or inflammatory diseases, in particular presenting cutaneous or mucocutaneous lesions.

FIG. 8. Systemic treatment of skin damage in MRL/lpr mice with the arsenic compound $As_2O_5$. Changes in inflammatory lesions of skin tissue in two male MRL/lpr mice (FIG. 8A) and two female mice (FIG. 8B) treated each week with 5 intraperitoneal injections of 0.1 ml per 10 g of mouse of a solution of arsenic $As_2O_5$ at the concentration of 0.5 mg/ml.

The invention discloses means for overcoming the disadvantages of the prior art, in particular the side effects on the immune system and the rebound effect observed in the treatments of the prior art. Indeed, the Inventors have discovered, unexpectedly, that the arsenic compound $As_2O_5$ proves to be an excellent effective active ingredient and has no side effects in the treatment and/or prevention of skin lesions associated with autoimmune and/or inflammatory diseases.

This medical use is all the more surprising since the toxicity of the arsenic compound $As_2O_5$ for man is well-known, the oral lethal dose for man being evaluated at 5-50 mg/kg, or between 7 drops and 1 teaspoon for a subject weighing about 75 kilos. Chronic exposure can cause nerve damage in the extremities, change the cellular composition of the blood and cause structural changes in blood components. The arsenic compound $As_2O_5$ has been described as an irritant of the eyes, nose and throat, and it appears a priori evident that it would be contraindicated in the case of dermatological problems.

According to a first aspect, the invention relates to an arsenic compound $As_2O_5$ for use in the treatment and/or prevention of skin lesions associated with autoimmune and/or inflammatory diseases in a human subject.

In other words, the invention relates to the use of the arsenic compound $As_2O_5$ for the preparation of a medicinal product for treating and/or preventing skin lesions associated with autoimmune and/or inflammatory diseases in a human subject, and to a method for preventing and/or treating skin lesions associated with autoimmune and/or inflammatory diseases comprising the administration of the arsenic compound $As_2O_5$ to a human subject In particular, the target will be skin lesions associated with autoimmune and/or inflammatory diseases selected from, in particular, lupus erythematosus, scleroderma, psoriasis, cutaneous vasculitis, vascular purpura, autoimmune bullous dermatoses (in particular bullous pemphigoid, cicatricial pemphigoid, linear IgA dermatosis, dermatitis herpetiformis, epidermolysis bullosa acquisita, pemphigus and variants thereof), dermatitis, (in particular atopic dermatitis, seborrheic dermatitis, stasis dermatitis), dermatomyositis, erythema nodosum, pyoderma gangrenosum, eczema (in particular eczema atopic, contact eczema, dyshidrotic eczema), lichen planus, lichen sclerosus et atrophicus, and alopecia areata. Preferentially the skin lesions associated with autoimmune or inflammatory diseases are skin lesions associated with lupus.

In the context of the present invention, the term "lupus" is equivalent to the term "lupus erythematosus" and comprises cutaneous lupus erythematosus (CLE) and disseminated lupus erythematosus (DLE) or systemic lupus erythematosus (SLE). CLE is a particularly polymorphic affection traditionally divided into three groups: chronic CLE, which includes discoid lupus, tumid lupus, lupus pernio and lupus profundus (or panniculitis); subacute CLE (SCLE); and acute CLE (ACLE).

The arsenic compound is particularly advantageous in that it does not induce an undesirable effect or a rebound effect. It is thus particularly indicated in specific subject populations as an alternative to corticosteroid therapy, such as nonresponsive subjects or subjects presenting tachyphylaxis to cortisone.

The arsenic compound $As_2O_5$, or arsenic pentoxide, is widely used as herbicide and as wood preservative and in the manufacture of colored glass. It is thus easy for the skilled person to procure this compound, which can also be synthesized from the compound $As_2O_3$, or arsenic trioxide, according to well-known methods.

According to a second aspect, the invention relates to a composition comprising an arsenic compound $As_2O_5$, preferentially for treating and/or preventing skin lesions associated with autoimmune diseases in a human subject.

The compound and the composition of the present invention can be administered by a variety of methods of administration, including systemic administration and topical administration. The compound and the composition of the present invention can be administered, for example, by general route (systemic administration), which includes oral route, parenteral route, nasal route, rectal route or pulmonary route, or locally (topical administration). The skilled person will understand that particular formulations may be envisioned according to the method of administration selected.

The composition of the invention is preferentially in a form suitable for topical administration, in particular dermatological administration. It can advantageously be in all dosage forms normally used for topical application, in particular in the form of an aqueous, hydroalcoolic or oily solution, an oil-in-water or water-in-oil or multiple emulsion, an aqueous or oily gel, a liquid, paste or solid anhydrous product, a dispersion of oil in an aqueous phase using spherules (nanospheres, nanocapsules, lipid vesicles), a transdermal device or a device in any other form for topical application.

This composition can be more or less fluid and have the appearance of a cream, an ointment, a milk, a lotion, a serum, a paste, a foam or a gel. It can, optionally, be applied to the skin in aerosol form. It can also be in solid form and, for example, in stick form. It can also be applied by means of a patch.

In the context of topical application, this composition can further comprise a pharmaceutically acceptable carrier or excipient, in particular a pharmaceutically acceptable carrier or excipient for topical administration, in particular a dermatologically acceptable carrier or excipient, i.e., a support compatible with the skin. Preferably, an excipient suitable for topical administration is used, advantageously an excipient suitable for dermatological administration is used.

The dermatologically acceptable excipients can be any excipient among those known to the skilled person for purposes of obtaining a composition for topical application in the form of a cream, a lotion, a gel, an ointment, an emulsion, a microemulsion, a spray, etc.

The composition according to the invention can in particular contain additives and formulation aids such as water, fats, surfactants (emulsifiers and detergents), thickeners, gelling agents, humectants, leveling agents, stabilizers, dyes, fragrances and preservatives (antioxidant, bactericide or bacteriostatic). Suitable emulsifiers comprise, for example, stearic acid, trolamine or triethanolamine, PEG-40-stearate.

According to another embodiment of the invention, the composition is in a form suitable for systemic administration, in particular parenteral administration. It can advantageously be in all dosage forms normally used for parenteral application, in particular in the form of a liquid solution, in particular an aqueous solution. Preferentially, the composition in a form suitable for parenteral administration is sterile. Preferentially, the composition in a form suitable for parenteral administration is apyrogenic. By "apyrogenic" is meant, in the context of the invention, that the composition according to the invention does not cause fever in the subject in the 48 hours following its administration. Preferentially, the composition in a form suitable for parenteral administration is clear. By "clear" is meant, in the context of the present invention, that it does not comprise suspended particles upon visual inspection. As need be, or to prevent possible particulate contamination, the composition will be filtered through a sterile 0.22 μm filter. Thus, according to a particular embodiment, the composition in a form suitable for parenteral administration is filtered through a sterile filter whose pores have a size allowing to pass only molecules 0.22 μm or smaller. Preferentially, the composition in a form suitable for parenteral administration has a pH between 7.3 and 7.5.

The parenteral administration can be carried out by injecting the composition of the invention via any route, for example by subcutaneous, intradermal, intramuscular, intravenous, intraperitoneal, intravascular routes or intra-arterial injection. The injections can be given with conventional syringes and needles, or with other suitable devices available in the art.

The methods of administration, dosing schedules and optimal dosage forms of the compositions and compositions of the invention can be determined according to the criteria generally considered when establishing a pharmaceutical treatment, in particular a topical and/or dermatological treatment, adapted to a patient, such as, for example, the patient's age or weight, the seriousness of their general condition, tolerability of the treatment, side effects observed.

The therapeutic dose used to treat mucocutaneous lesions varies according to the seriousness or the extent of the lesions and according to the treatment conditions. Thus, the dose, and if need be the frequency, can be adapted according to age and body weight and to the extent and age of the lesions. Moreover, the dose and the frequency of administration can be adapted so as to obtain a given effective amount. According to a preferred embodiment of the invention, the daily effective amount corresponds to 0.01 to 5 mg of the arsenic compound $As_2O_5$ per kg of body weight of the subject, preferably 0.025 to 0.75 mg of the arsenic compound $As_2O_5$ per kg of body weight of the subject.

The composition in a form suitable for topical administration is typically administered daily, for a period of 5 to 60 days at a concentration in arsenic compound $As_2O_5$ varying from 0.5 mg (or 0.05%) to 50 mg (or 5%) per ml or g of composition. According to a preferred embodiment of the invention, the daily effective amount in the case of topical administration corresponds to 0.05 to 5 mg of the arsenic compound $As_{2O5}$ per kg of body weight of the subject, preferably 0.1 to 0.5 mg of the arsenic compound $As_2O_5$ per kg of body weight of the subject. The total amount of composition applied daily depends on the surface area of the skin to be treated. Preferentially, the daily total amount is less than or equal to 1 mg of the arsenic compound $As_2O_5$ per kg of body weight of the subject. It is possible to carry out successive treatments, advantageously separated by 1 to 4 weeks during which the subject is not treated.

The treatment is preferentially carried out over 5 days. The dosing schedule could, however, be reduced in the case of smaller tissue lesions. Moreover, after a front-line treatment with a high concentration of the arsenic compound $As_2O_5$ alone or in combination with $As_2O_3$, the doses could be spaced apart, even with breaks in treatment of 1 to 8 weeks depending on the case.

The composition in a form suitable for parenteral administration is typically administered daily, for a period of 5 to 30 days. It is possible to carry out successive treatments, advantageously separated by 1 to 8 weeks during which the subject is not treated. The daily effective amount in the case of parenteral administration is 0.01 to 1 mg of the arsenic compound $As_2O_5$ per 1 kg of body weight of the subject, preferably 0.025 to 0.75 mg of the arsenic compound $As_2O_5$ per 1 kg of body weight of the subject. Preferentially, the composition of the invention comprises between 0.01% and 0.15% of the arsenic compound $As_2O_5$ relative to the total weight of the composition.

Moreover, the arsenic compound $As_2O_5$ can be administered, if need be, with other active ingredients contributing to the treatment of the targeted pathologies, for the purpose of improving the therapeutic response of the subject.

Thus, according to a particular embodiment, the composition of the invention further comprises at least one compound selected from corticoids, tacrolimus, hydroxychloroquine, chloroquine, thalidomide, methotrexate, compounds having anti-TNF action, compounds having anti-CD20 action, compounds having anti-BAFF action, compounds having anti-IL1 action, compounds having anti-IL-6 action.

A certain number of arsenic compounds have shown their advantage in the treatment of autoimmune diseases, in particular lupus (EP 1 499 330). Thus, the arsenic compound $As_2O_5$ can be administered in combination with other arsenic compounds contributing to the treatment of autoimmune and/or inflammatory pathologies.

According to another particular embodiment, the composition of the invention further comprises at least one compound selected from the arsenic compounds $As_2O_3$, $As_4O_6$, $As_2S_2$, $As_2S_3$, $As_2S_5$ and $As_4S_4$. Preferentially, the composition of the invention comprising an arsenic compound $As_2O_5$ further comprises at least the arsenic compound $As_2O_3$.

In other words, according to another embodiment, the composition of the invention comprises a combination of arsenic compounds, said combination comprising the arsenic compound $As_2O_5$ and in addition at least one arsenic compound selected from the list consisting of $As_2O_3$, $As_2O_5$, $As_4O_6$, $As_2S_2$, $As_2S_3$, $As_2S_5$ and $As_4S_4$. Advantageously, said combination comprises the arsenic compound $As_2O_5$ and the additional arsenic compound $As_2O_3$. Still more advantageously, said combination consists of the arsenic compound $As_2O_5$ and the additional arsenic compound $As_2O_3$.

The water solubility of the various inorganic arsenic compounds varies considerably. For example, the arsenic compound $As_2O_3$ is poorly soluble in water (37 g/l at 20° C.) or in alcohol, and thus formulating it proves difficult. The Inventors have discovered that the solubility of the arsenic compound $As_2O_3$ can be modified by varying the oxidation-reduction, pH and temperature conditions during the preparation of the composition. For example, to circumvent the problem of the low water solubility of the compound $As_2O_3$, it is first dissolved at a high concentration (60 to 70 mg/ml) in dilute alkaline solution (0.5 M or 1 M) and gently heated until a clear, colorless solution is obtained.

Thus, according to a particular embodiment of the invention, the composition of the invention further comprises at least the arsenic compound $As_2O_3$ and is characterized in that the compound $As_2O_3$ in said composition is able to be obtained by a method comprising a step of dissolution in alkaline solution. In the context of the present invention, the words "alkaline solution" refer to any basic solution, i.e., any solution the pH of which is greater than 7.

The clear $As_2O_3$ solution can further be made free of particles and sterile by means of filtration, according to any technique well-known to the skilled person. The clear $As_2O_3$ solution thus obtained can further be diluted in phosphate buffer or sterile physiological saline at the concentration varying from 0.5 to 1.5 mg/ml for use in vivo.

Preferentially, the composition of the invention comprises between 0.01% and 0.15% of the arsenic compound $As_2O_5$ relative to the total weight of the composition, and between 0.05% and 5% of the arsenic compound $As_2O_3$ relative to the total weight of the composition.

It will appear obvious to the skilled person that the combined administration of several active ingredients can be carried out, according to the targeted pathologies and their seriousness, by the joint administration of these compounds, or alternatively by alternating the administration of each separately, for example.

According to a particular embodiment, the invention relates to products containing an arsenic compound $As_2O_5$ and at least one compound selected from corticoids, tacrolimus, hydroxychloroquine, chloroquine, thalidomide, methotrexate, compounds having anti-TNF action, compounds having anti-CD20 action, compounds having anti-BAFF action, compounds having anti-IL1 action, compounds having anti-IL-6 action as a combination product for simultaneous, separate or sequential use in the treatment and/or prevention of skin lesions associated with autoimmune diseases in a human subject.

According to a particular embodiment, the invention relates to products containing an arsenic compound $As_2O_5$ and at least one arsenic compound selected from the arsenic compounds $As_2O_3$, $As_4O_6$, $As_2S_2$, $As_2S_3$, $As_2S_5$ and $As_4S_4$, as a combination product for simultaneous, separate or sequential use in the treatment and/or prevention of skin lesions associated with autoimmune diseases in a human subject. In other words, the invention also relates to products containing an arsenic compound $As_2O_5$ and an additional arsenic compound selected from the list consisting of $As_2O_3$, $As_2O_5$, $As_4O_6$, $As_2S_2$, $As_2S_3$, $As_2S_5$ and $As_4S_4$ as a combination product for simultaneous, separate or sequential use in the treatment and/or prevention of skin lesions associated with autoimmune diseases in a human subject. Preferentially, said products of the invention contain an arsenic compound $As_2O_5$ and the additional arsenic compound $As_2O_3$.

In other words, the invention relates to the use of products containing an arsenic compound $As_2O_5$ and at least one arsenic compound selected from the arsenic compounds $As_2O_3$, $As_4O_6$, $As_2S_2$, $As_2S_3$, $As_2S_5$ and $As_4S_4$, as a combination product for simultaneous, separate or sequential use for the preparation of a medicinal product for treating and/or preventing skin lesions associated with autoimmune and/or inflammatory diseases in a human subject.

Moreover, the invention relates to a method for preventing and/or treating skin lesions associated with autoimmune and/or inflammatory diseases comprising the simultaneous, separate or sequential administration of the arsenic compound $As_2O_5$ and at least one arsenic compound selected from the arsenic compounds $As_2O_3$, $As_4O_6$, $As_2S_2$, $As_2S_3$, $As_2S_5$ and $As_4S_4$ to a human subject. According to a particular embodiment, the invention relates to a method for preventing and/or treating skin lesions associated with autoimmune and/or inflammatory diseases comprising the administration of the compound $As_2O_5$ alternating with the administration of at least one arsenic compound selected from the arsenic compounds $As_2O_3$, $As_4O_6$, $As_2S_2$, $As_2S_3$, S $As_2S_5$, and $As_4S_4$.

In other words, the invention also relates to a method for treating and/or preventing skin lesions associated with autoimmune and/or inflammatory diseases in a human subject, comprising a step of administering to said subject a composition or products according to the invention. Preferentially, in the context of the method of the invention, the application of $As_2O_5$ is alternated with the administration of at least one additional arsenic compound selected from the list consisting of $As_2O_3$, $As_2O_5$, $As_4O_6$, $As_2S_2$, $As_2S_3$, $As_2S_5$ and $As_4S_4$. Advantageously, in the context of the method of the invention, the application of $As_2O_5$ is alternated with the administration of the arsenic compound $As_2O_3$.

The combined administration of the arsenic compound $As_2O_5$ and the arsenic compound $As_2O_3$ in particular makes it possible to circumvent possible resistance of the subject to one or the other of these arsenic salt compounds, to the extent that their mechanisms of action are different.

According to a preferred embodiment, the invention relates to products containing an arsenic compound $As_2O_5$ and an arsenic compound $As_2O_3$ as a combination product for simultaneous, separate or sequential use in the treatment and/or prevention of skin lesions associated with autoimmune diseases in a human subject.

Preferentially, the products containing an arsenic compound $As_2O_5$ and an arsenic compound $As_2O_3$ as a combination product are administered at a daily dose for the arsenic compound $As_2O_5$ of between 0.01 and 0.2 mg per kg of body weight of the subject and at a daily dose of the arsenic compound $As_2O_3$ of between 0.01 and 0.2 mg per kg of body weight of the subject.

The invention also relates to sets or kits comprising at least one container containing the arsenic compound $As_2O_5$ in a form pharmaceutically acceptable for topical and/or dermatological administration, and advantageously an information leaflet or package insert. The kit can further comprise a container containing the arsenic compound $As_2O_3$. The kit can further comprise suitable means of application such as a graduated pipette, a syringe, a spatula, a brush or compresses, for example.

The Inventors have thus discovered, in a particularly surprising manner, that the topical treatment of skin lesions associated with autoimmune and/or inflammatory diseases in a human subject, without notable side effects, could advantageously use i. at least the compound $As_2O_5$, optionally combined with other arsenic compounds, as described above, or, alternatively, ii. one or more of said other arsenic compounds.

The topical use of such compounds, however, appeared counterintuitive to the extent that these compounds are known for their high toxicity, and in particular their irritant nature, the cause of contact dermatitis and other mucosal irritations.

Thus, according to another aspect, the invention relates to an arsenic compound selected from $As_2O_3$, $As_2O_5$, $As_4O_6$, $As_2S_2$, $As_2S_3$, $As_2S_5$ and $As_4S_4$, for use in the topical treatment and/or prevention of skin lesions associated with autoimmune and/or inflammatory diseases in a human subject.

In other words, the invention relates to the use of an arsenic compound selected from $As_2O_3$, $As_2O_5$, $As_4O_6$, $As_2S_2$, $As_2S_3$, $As_2S_5$ and $As_4S_4$, for the preparation of a medicinal product for the topical treatment and/or prevention of skin lesions associated with autoimmune and/or inflammatory diseases in a human subject, as well as a method of topical prevention and/or treatment of skin lesions associated with autoimmune and/or inflammatory diseases comprising the administration of an arsenic compound selected from $As_2O_3$, $As_2O_5$, $As_4O_6$, $As_2S_2$, $As_2S_3$, $As_2S_5$ and $As_4S_4$ to a human subject.

It is understood in the context of the invention that the target will be the same pathologies as those cited above, namely skin lesions associated with autoimmune or inflammatory diseases selected from lupus erythematosus, scleroderma, psoriasis, cutaneous vasculitis, vascular purpura, autoimmune bullous dermatoses (in particular bullous pemphigoid, cicatricial pemphigoid, linear IgA dermatosis, dermatitis herpetiformis, epidermolysis bullosa acquisita, pemphigus and variants thereof), dermatitis, (in particular atopic dermatitis, seborrheic dermatitis, stasis dermatitis), dermatomyositis, erythema nodosum, pyoderma gangrenosum, eczema (in particular atopic eczema, contact eczema, dyshidrotic eczema), lichen planus, lichen sclerosus et atrophicus, and alopecia areata. Preferentially the skin lesions associated with autoimmune or inflammatory diseases are skin lesions associated with lupus.

The topical administration of the arsenic compounds is facilitated by the use of compositions specially adapted to this use. Indeed, it is well-known that the formulation of a composition is a determining factor for guaranteeing the satisfactory administration and the efficacy of an active product. This is particularly true in the case of arsenic, which exists in a wide variety of compounds with different physicochemical properties.

According to another aspect, the invention relates to a topical composition, in particular a dermatological composition, comprising at least one arsenic compound selected from $As_2O_3$, $As_2O_5$, $As_4O_6$, $As_2S_2$, $As_2S_3$, $As_2S_5$ and $As_4S_4$, in particular for use in the treatment and/or prevention of skin lesions associated with autoimmune diseases in a human subject.

The invention also relates to sets or kits comprising at least one container containing at least one arsenic compound selected from $As_2O_3$, $As_2O_5$, $As_4O_6$, $As_2S_2$, $As_2S_3$, $As_2S_5$ and $As_4S_4$ in a form pharmaceutically acceptable for topical and/or dermatological administration. The kit can also comprise suitable means of application such as a graduated pipette, and/or a spatula.

MRL/lpr mice spontaneously develop disseminated lupus erythematosus, rheumatoid polyarthritis and Sjögren's syndrome characterized by dermatological, vascular, renal, pulmonary, articular and ocular damage due to lymphoid cell infiltrates. As in man, a strong sexual dimorphism is observed in MRL/lpr mice, the female mice presenting an earlier and more severe pathology than the males and dying earlier. The disease begins around the age of 8 weeks and causes the death of the mice, on average, at around 18 weeks of age for the females and 22 weeks for the males, the average lifespan of a normal mouse being 2 years.

Experiment 1: Demonstration of the therapeutic efficacy of the arsenic compound $As_2O_3$ for the local treatment of skin damage in MRL/lpr mice and of its satisfactory tolerance at the therapeutic doses envisaged.

Goal: This experiment aims to evaluate the therapeutic efficacy and the tolerance of a topical treatment of severe skin lesions of autoimmune MRL/lpr mice with arsenic trioxide or $As_2O_3$. It also aims to evaluate the possibility of adapting the dosing schedule depending on the severity of the tissue damage. Lastly, it also aims to evaluate the speed of the treatment using mice considered "old" with regard to the limited lifespan of MRL/lpr mice and thus likely to die before the efficacy of the treatment could be observed.

Methods: The solubility of arsenic compounds depends mainly on the pH and oxidation-reduction conditions and the temperature of the excipient. Since the arsenic compound $As_2O_3$ is poorly water soluble, it is first dissolved at a high concentration (60 to 70 mg/ml) in dilute alkaline solution (0.5 or 1 M) and gently heated until a clear and colorless solution is obtained. This solution is made free of particles and sterile by filtration on a 0.22 μm filter. The stock $As_2O_3$ solution thus obtained is then diluted in phosphate buffer or sterile physiological saline at the concentration varying from 0.5 mg/ml for use in vivo. The stock solution of the arsenic compound $As_2O_3$ is preserved from 1 to 3 months in the refrigerator (4° C.), whereas the dilute solution is preserved only 5 days at 4° C. and away from light.

MRL/lpr mice (10 females and 10 males per group, aged 4 to 5 months) presenting severe lupus-type skin lesions, and for some cutaneous necrotizing vasculitis, were treated, 3 or 5 times per week depending on the experiment (from Monday to Friday), for 8 weeks, by application on the tissue lesions of a compress (or a brush) impregnated with arsenic $As_2O_3$ solution at concentrations of 0.5 mg/ml. The control animals were mice, of the same age and sex, treated with the excipient.

Results: The photographs in FIGS. 1 and 2 are characteristic of the type and of the extent of the skin lesions observed in a female MRL/lpr mouse (FIG. 1) and a male MRL/lpr mouse (FIG. 2) at the beginning of the treatment (t0) and after 2, 4 and 8 weeks of topical treatment with the arsenic compound $As_2O_3$ with 5 applications/week.

Figure 1:
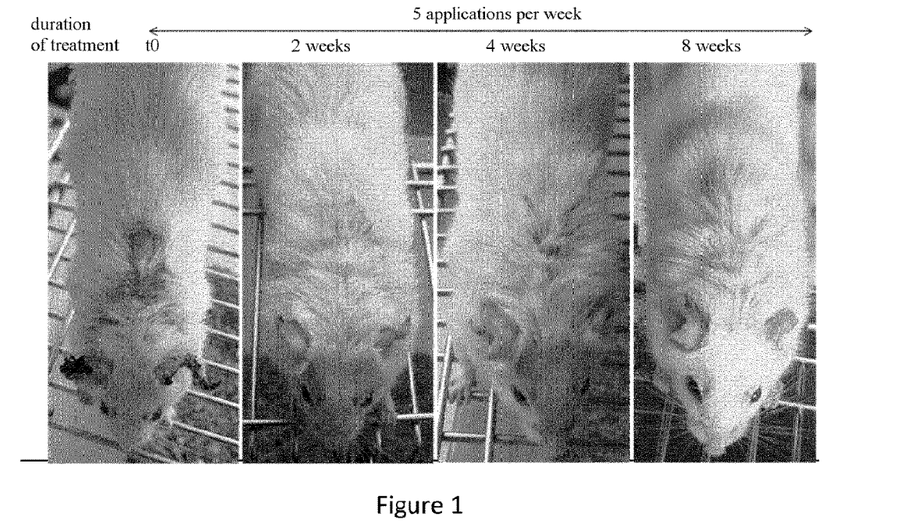
FIG. 1. Topical treatment of skin damage in MRL/lpr mice with the arsenic compound $As_2O_3$. Changes in inflammatory lesions of skin tissue, cutaneous necrotizing vasculitis and alopecia in a female MRL/lpr mouse after 2, 4 and 8 weeks of topical treatment with 5 weekly applications of the arsenic compound $As_2O_3$ at the concentration of 0.5 mg/ml.
Figure 2:
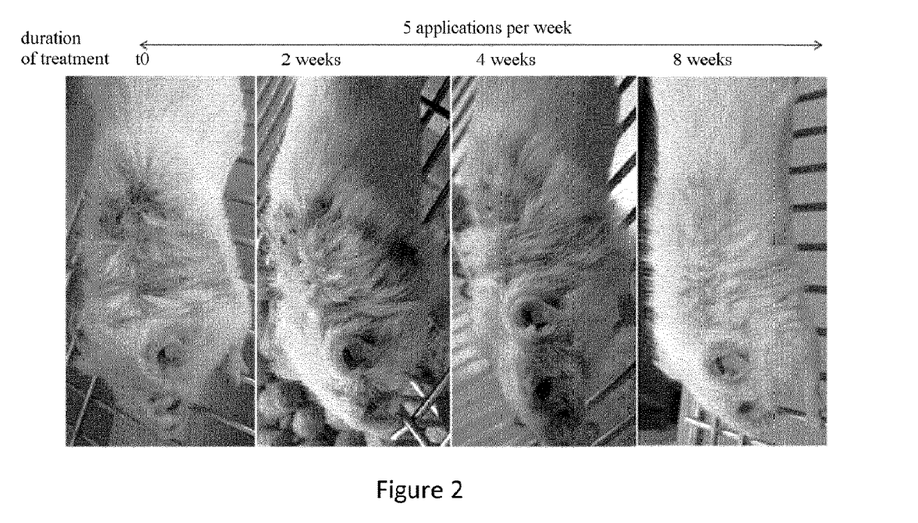
FIG. 2. Topical treatment of skin damage in MRL/lpr mice with the arsenic compound $As_2O_3$. Changes in inflammatory lesions of skin tissue in a male MRL/lpr mouse after 2, 4 and 8 weeks of topical treatment with 5 weekly applications of the arsenic compound $As_2O_3$ at the concentration of 0.5 mg/ml.

After 2 weeks of treatment, the tissue destruction ceased and even regressed, in particular concerning the ear necrosis characteristic of cutaneous vasculitis of the vessels (FIG. 1). After 8 weeks of treatment, the inflammatory skin lesions are observed to nearly completely disappear, even leading to the regrowth of hair. No undesirable effect (nonspecific immunosuppression, tissue toxicity or premature death) was observed in the animals treated with the arsenic compound $As_2O_3$, indicating satisfactory tolerance at the therapeutic doses used. Moreover, the large majority of the animals lived nearly 8 weeks after the beginning of the treatment, which is considerable with regard to the average lifespan of MRL/lpr mice. Conversely, a large number of control animals died during the experiment and all the surviving animals presented severe skin lesions after 8 weeks of treatment with the excipient.

Figure 3:
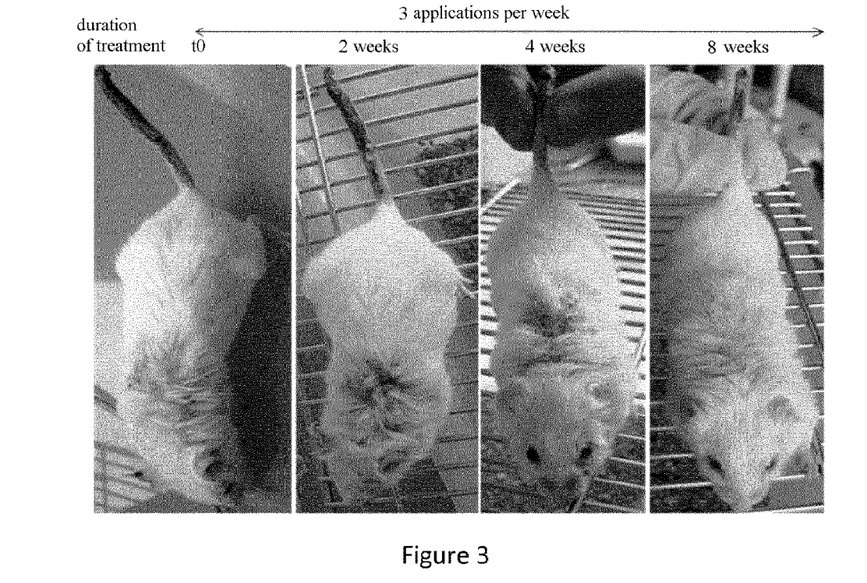
FIG. 3. Topical treatment of skin damage in MRL/lpr mice with fewer applications of the arsenic compound $As_2O_3$. Changes in inflammatory lesions of skin tissue and cutaneous necrotizing vasculitis in a female MRL/lpr mouse after 2, 4 and 8 weeks of topical treatment with the arsenic compound $As_2O_3$, at the concentration of 0.5 mg/ml, in 3 weekly applications.

The disease being able to appear in more or less severe forms, it is necessary to adapt the dosing schedule. In the experiment illustrated by FIG. 3, the number of weekly topical applications of the arsenic compound $As_2O_3$ was reduced to 3 (Monday, Wednesday, Friday) in MRL/lpr mice whose skin lesions were less severe than those of the animals presented in FIGS. 1 and 2. Changes in the skin lesions during this treatment were, as before, monitored for 8 weeks. As shown in the photographs of FIG. 3, a significant decrease in tissue lesions was observed in female MRL/lpr mice after 8 weeks of treatment with 3 weekly applications of the arsenic compound $As_2O_3$ instead of 5 for FIGS. 1 and 2. It is thus quite possible to modulate the dosing schedule according to seriousness of the lesions observed at the beginning of the treatment.

Conclusions: This experiment shows that the arsenic compound $As_2O_3$ has high therapeutic efficacy via topical application in the treatment of severe inflammatory lesions of skin tissue, cutaneous necrotizing vasculitis and alopecia. Moreover, it enables complete regeneration of skin tissue, objectified by nearly complete regrowth of hair. The arsenic compound $As_2O_3$ used topically also shows a great speed of action since, after 2 weeks of treatment, the destruction of skin tissue had ceased, even regressed. For the less severe forms of the disease, the number of weekly applications can be decreased without a significant loss of efficacy. In addition, the majority of the animals treated with the arsenic compound $As_2O_3$ lived more than 8 weeks after the beginning of the treatment without presenting notable undesired effects, indicating that the arsenic compound $As_2O_3$ is tolerated well at the therapeutic doses used and that this topical treatment has a large positive effect on the longevity of MRL/lpr mice. Indeed, at the conclusion of this experiment, the animals treated with the arsenic compound $As_2O_3$ were 24 to 28 weeks of age, whereas they generally die at between 18 and 22 weeks of age.

Experiment 2: Therapeutic range and gradual decrease in the number of weekly topical applications of the arsenic compound $As_2O_3$ Goal: This experiment aims to evaluate the possibility of a gradual decrease in the number of applications per week of the arsenic compound $As_2O_3$ without altering the efficacy of the topical treatment. This spacing of doses proves necessary when high doses were used during the front-line treatments or when undesirable effects occur in a patient during long-term treatment.

Methods: Severe skin lesions and cutaneous necrotizing vasculitis present before treatment (time t0 in FIGS. 3, 4 and 5) in 15 4-month-old MRL/lpr mice were treated by applying a compress (or a brush) impregnated with a solution of the arsenic compound $As_2O_3$ at the concentration of 0.5 mg/ml. The number of applications per week varied from 2 to 5 depending on the experiment. Similarly, the total duration of the topical treatment varied from 7 to 32 weeks.

Figure 4:
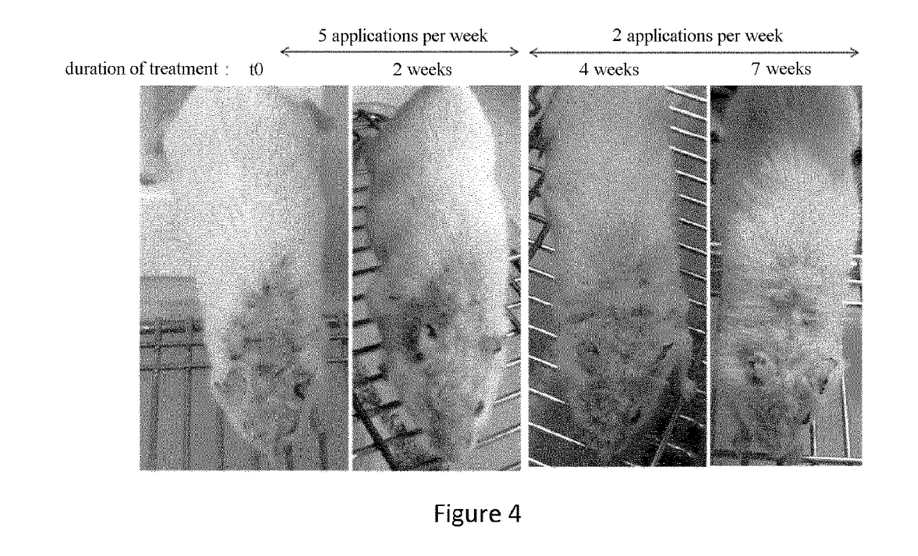
FIG. 4. Gradual decrease in the number of weekly topical applications of the arsenic compound $As_2O_3$. Changes in inflammatory lesions of skin tissue in an MRL/lpr mouse treated with the arsenic compound $As_2O_3$, at the concentration of 0.5 mg/ml, first in 5 applications per week for 2 weeks and then 2 applications per week for a further 5 weeks.

Results: Five weekly applications (Monday to Friday) of the arsenic compound $As_2O_3$ at the concentration of 0.5 mg/ml halts the progression of the tissue lesions in 2 to 4 weeks depending on the severity of the lesions present at time t0. We thus evaluated the consequences of a decrease in the number of applications per week of the arsenic compound $As_2O_3$. In the example presented in FIG. 4, the number of topical applications was reduced to 2 per week (Monday and Thursday) for 5 weeks. FIG. 4 shows that not only did this reduction not lead to a recurrence of tissue destruction but that skin damage decreased considerably after 7 weeks of topical treatment.

Figure 5:
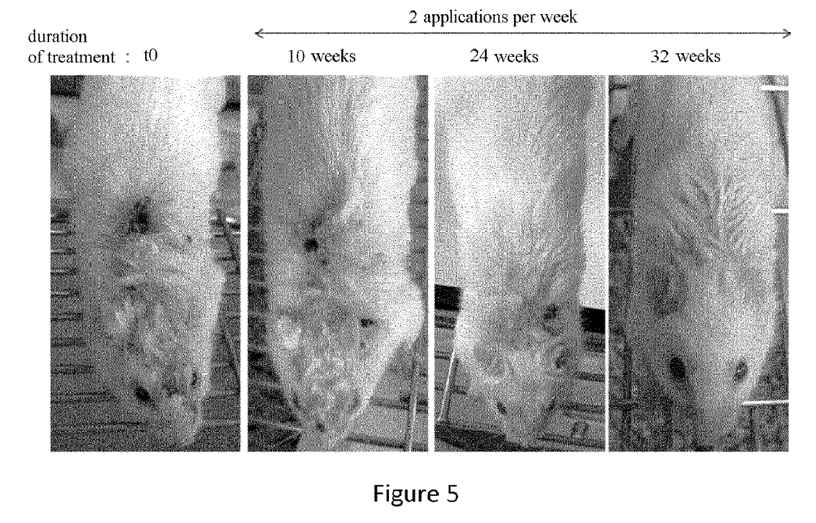
FIG. 5. Topical treatment with the arsenic compound $As_2O_3$ leads to a significant increase in lifespan. Changes in inflammatory lesions of skin tissue in a female MRL/lpr mouse treated discontinuously for 32 weeks with the arsenic compound $As_2O_3$. After 4 weeks of treatment, in 5 applications per week, the number of applications per week of the arsenic compound $As_2O_3$ was first reduced to 3 for 6 weeks and then to 2 for a further 22 weeks.

The results presented in FIG. 5 are another example showing that it is possible to modulate, during the treatment, the number of weekly topical applications of the arsenic compound $As_2O_3$. Thus, a female MRL/lpr mouse was first treated for 4 weeks with 5 weekly applications (Monday to Friday). Once the development of the tissue lesions halted, the number of weekly application was reduced to 3 (Monday, Wednesday, Friday). Since no relapse or rebound of the disease was observed after 6 new weeks of treatment with this reduced dosing schedule, the number of weekly applications was reduced again, to 2 (Monday and Thursday), for a further 22 weeks. During the 32 weeks the treatment lasted, periods without treatment of 10 or so days were introduced. It is important to recall that MRL/lpr mice die between the ages of 4 and 5 months. However, the MRL/lpr mouse shown in FIG. 5, which was 3.5 months old at the beginning of the treatment (t0), lived until the age of 1 year, the date it was euthanized.

Conclusion: Once the progression of the tissue lesions is stopped with a front-line treatment consisting of 5 applications per week of the arsenic compound $As_2O_3$, a spacing of doses can then be envisaged by reducing the number of applications per week to 3, even to 2, for several weeks without altering the efficacy of the topical treatment. The absence of relapse or rebound of the disease after reducing the dosing schedule shows the high efficacy of topical $As_2O_3$ as well as its wide therapeutic range. In addition, this experiment shows, as did the previous experiment, that topical treatment with the arsenic compound $As_2O_3$ has a positive effect on the longevity of MRL/lpr mice.

Experiment 3: Demonstration of the therapeutic efficacy of the arsenic compound $As_2O_5$ for the local treatment of skin damage in MRL/lpr mice and its satisfactory tolerance at the doses envisaged.

Goal: The great etiological diversity of autoimmune and/or inflammatory diseases necessitates the development of a more varied therapeutic arsenal, in particular by means of molecules acting by different mechanisms. In the case of medicinal products based on arsenic compounds, we evaluated the therapeutic efficacy of arsenic pentoxide ($As_2O_5$) because its water solubility—and thus its method of preparation—and its mechanisms of action are different from those of arsenic trioxide, $As_2O_3$. Moreover, the toxicity of the arsenic compound $As_2O_5$ is lower than that of the compound $As_2O_3$ (about 1/60 the size), thus making it possible to reduce undesirable effects while retaining the therapeutic benefit, and even to increase the administered dose, if necessary. Experiment 3 thus aims to evaluate the therapeutic efficacy of the arsenic compound $As_2O_5$ for the topical treatment of severe skin lesions of autoimmune MRL/lpr mice and its lack of toxicity. It also aims to evaluate the speed of the treatment using mice suffering from severe tissue lesions at the beginning of the treatment and thus likely to die quickly during the experiment.

Methods: The arsenic compound $As_2O_5$ is first dissolved at a high concentration (10 to 15 mg/ml) in distilled water until a clear and colorless solution is obtained. The solution is made sterile and free of particles by filtration on a 0.22 μm filter. The stock $As_2O_5$ solution thus obtained is then diluted in phosphate buffer or sterile physiological saline so as to obtain a concentration between 0.5 mg/ml for use in vivo. The stock solution of the arsenic compound $As_2O_5$ is preserved for 1 to 3 months in the refrigerator (4° C.), while the dilute solution is preserved for only 5 days at 4° C. and away from light.

MRL/lpr mice (12 females and 12 males, 4 to 5 months of age) presenting severe lupus-type skin lesions, and for some cutaneous necrotizing vasculitis (time t0 in FIG. 6), were treated 5 times per week (Monday to Friday), for 8 weeks, by applying on the tissue lesions a compress (or a brush) impregnated with a solution of arsenic $As_2O_5$ at concentrations of 0.5 mg/ml. The control animals were mice of the same age and sex treated with the excipient.

Figure 6:
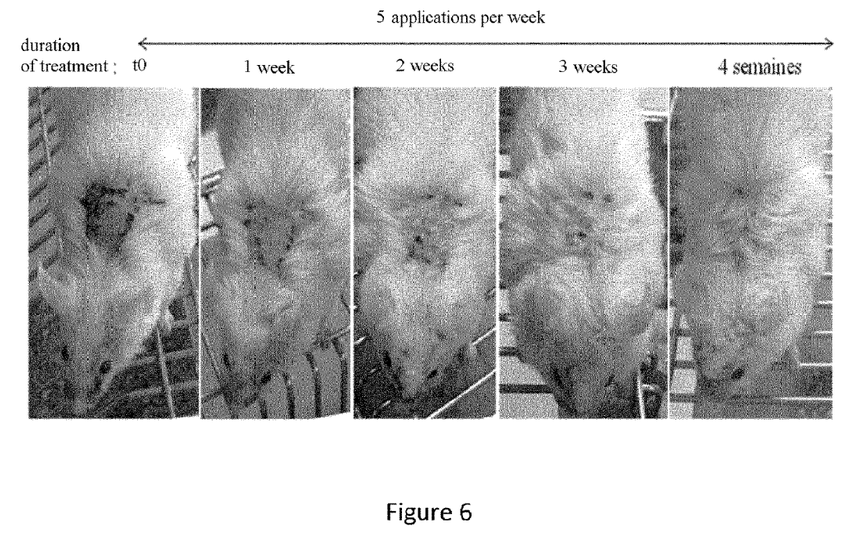
FIG. 6. Topical treatment of skin damage in MRL/lpr mice with the arsenic compound $As_2O_5$. Changes in inflammatory lesions of skin tissue in a male MRL/lpr mouse treated with 5 weekly applications of the arsenic compound $As_2O_5$ at the concentration of 0.5 mg/ml.

Results: FIG. 6 is an example illustrating the very high therapeutic efficacy of the arsenic compound $As_2O_5$ and its speed of action. Indeed, the photographs presented in FIG. 6 show that destruction of the skin had ceased as of the first week of treatment (consisting of 5 applications per week) and that they had almost disappeared after 4 weeks of treatment. Conversely, the control animals treated with the excipient continued to present severe skin lesions.

Conclusions: This experiment shows that the arsenic compound $As_2O_5$ has a high therapeutic efficacy via topical route in the treatment of severe inflammatory lesions of skin tissue, cutaneous necrotizing vasculitis and alopecia. It also induces regeneration of lesioned skin tissue, as shown by the nearly complete regrowth of hair. It also shows a quick speed of action since, in less than 2 weeks of treatment, the destruction of skin tissue had ceased, even regressed. Lastly, no undesirable effect related to nonspecific immunosuppression, tissue toxicity or premature death was observed in the animals treated with $As_2O_5$, indicating its satisfactory tolerance at the therapeutic doses used.

Experiment 4: Therapeutic range and gradual decrease in the number of weekly topical applications of the arsenic compound $As_2O_5$ Goal: This experiment aims to evaluate the possibility of a gradual decrease in the number of applications per week of the arsenic compound $As_2O_5$ without altering the efficacy of the topical treatment. This spacing of doses proves necessary following a front-line treatment at high doses or in the event of undesirable effects related to long-term treatment.

Methods: Severe skin lesions and cutaneous necrotizing vasculitis present at time t0 in 10 MRL/lpr mice 4 to 5 months in age were treated by applying a compress (or a brush) impregnated with a solution of the arsenic compound $As_2O_5$ at the concentration of 0.5 mg/ml. The number of applications per week was gradually reduced from 5 to 1 during the 10 weeks the treatment lasted.

Figure 7:
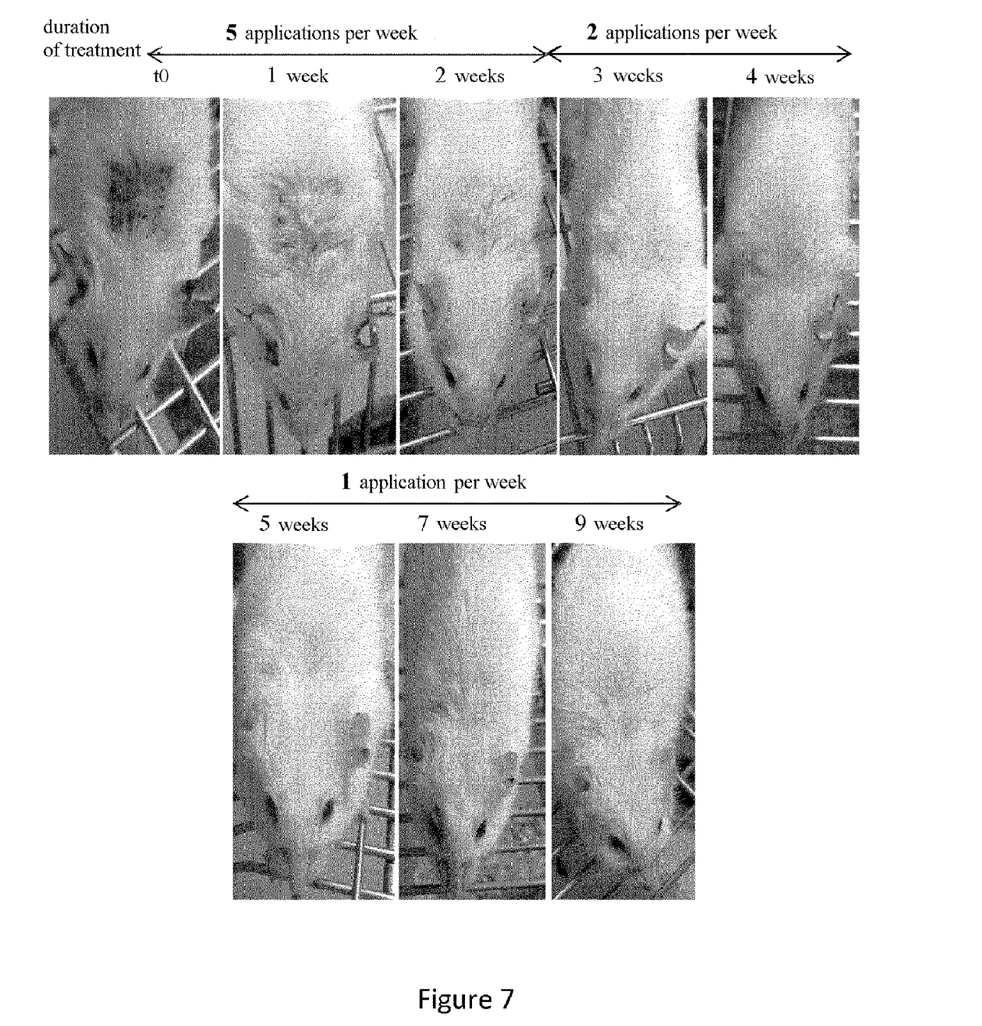
FIG. 7. Gradual decrease in the number of weekly topical applications of the arsenic compound $As_2O_5$. Changes in inflammatory lesions of skin tissue in a female MRL/lpr mouse treated with the arsenic compound $As_2O_5$ with, first, 5 applications per week for 2 weeks and then 2 weekly applications for 2 more weeks and finally a single weekly application for an additional 5 weeks.

Results: The animals were first treated with 5 weekly applications of $As_2O_5$ (Monday to Friday). As illustrated in FIG. 7, since the inflammatory lesions of the skin tissue itself and those of vasculitis had ceased after 2 weeks of treatment, we reduced the number of applications to 2 per week (Monday and Thursday). Since the skin lesions had nearly disappeared after 2 new weeks of treatment with this reduced dosing schedule, we decided to reduce it further and lower to 1 the number of applications per week (Monday) until the animals are euthanized. During the 5 weeks of treatment with a single application per week no relapse or rebound of the disease was observed.

Conclusion: This experiment confirms the high therapeutic efficacy and the speed of action of the arsenic compound $As_2O_5$ on severe inflammatory lesions of skin tissue. Indeed, the development of tissue lesions is generally stopped within 2 weeks with the front-line treatment consisting of 5 applications per week. Consequently, the doses can be quickly spaced apart. It was thus possible to reduce from 5 to 1 the number of applications per week without altering the efficacy of the topical treatment. The absence of relapse or rebound of the disease after this significant reduction in the dosing schedule shows the high efficacy of topical $As_2O_5$ and its wide therapeutic range. In addition, despite the large reduction in the dosing schedule, the majority of the animals treated with the arsenic compound $As_2O_5$ lived more than 8 weeks after the beginning of the treatment, indicating that this topical treatment has an evident positive effect on the longevity of MRL/lpr mice.

Experiment 5: Demonstration of the therapeutic efficacy of the arsenic compound $As_2O_5$ for the systemic treatment of skin damage in MRL/lpr mice and its satisfactory tolerance at the doses envisaged.

Goal: Experiment 5 aims to evaluate the therapeutic efficacy of the arsenic compound $As_2O_5$ administered systemically for the treatment of severe skin lesions of autoimmune MRL/lpr mice and its lack of toxicity.

Figure 8A:
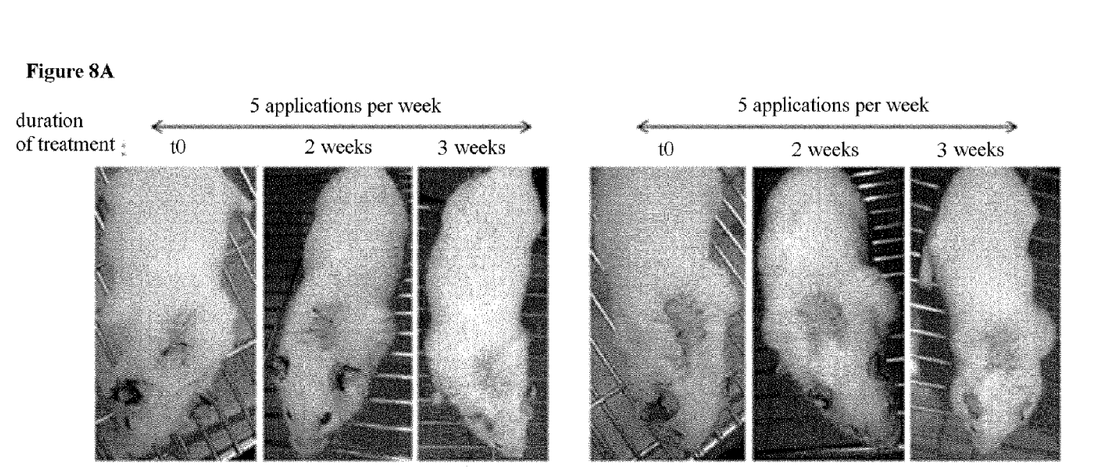
Figure 8B:
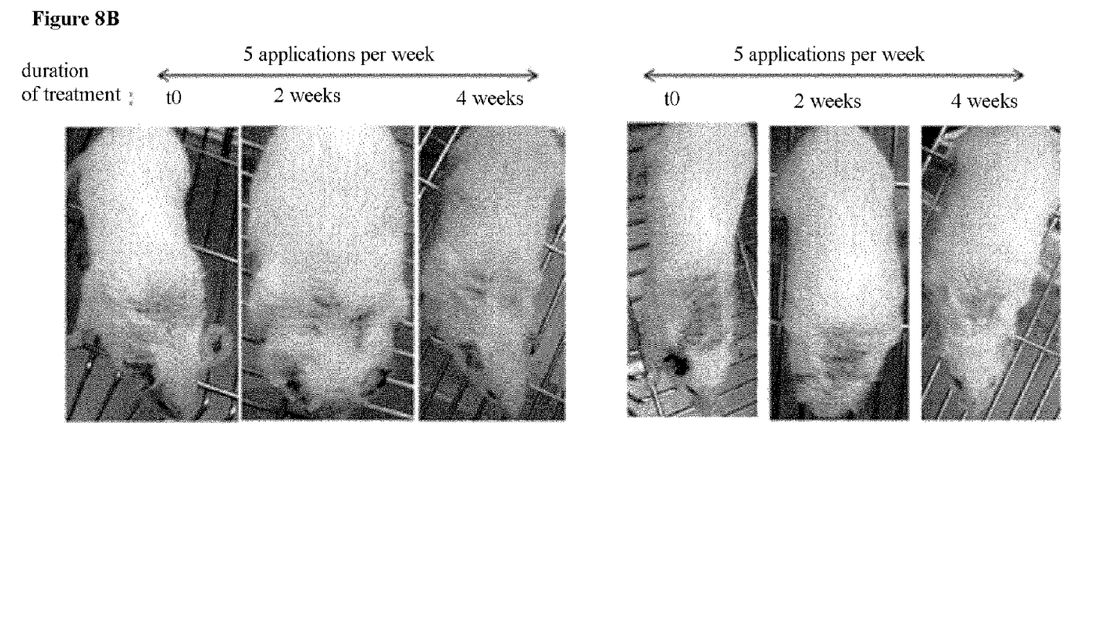

Methods: MRL/lpr mice (6 females and 6 males, 4 to 5 months of age) presenting severe lupus-type skin lesions and cutaneous necrotizing vasculitis (time t0 FIGS. 8A and 8B) were treated 5 times per week (Monday to Friday), for 3 or 4 weeks, by intraperitoneal injections of 0.1 ml per 10 g of mouse of a solution of arsenic $As_2O_5$ at the concentration of 0.5 mg/ml. The control animals were mice of the same age and sex treated with the excipient.

Results: FIG. 8 illustrates, in two male MRL/lpr mice (part A of the Figure) and two female MRL/lpr mice (part B), the high therapeutic efficacy of the arsenic compound $As_2O_5$ and its speed of action. Indeed, the photographs presented in FIG. 8 show that the destruction of skin had, depending on the initial severity of the lesions, strongly regressed or even nearly disappeared after 3 or 4 weeks of treatment. Conversely, the control animals treated with the excipient continued to present severe skin lesions.

Conclusions: This experiment shows that the arsenic compound $As_2O_5$ has a high therapeutic efficacy via systemic route in the treatment of severe inflammatory lesions of skin tissue, cutaneous necrotizing vasculitis and alopecia. It also induces regeneration of lesioned skin tissue, as shown by the nearly complete regrowth of hair. It also shows a quick speed of action since, in 3 to 4 weeks of treatment, the destruction of skin tissue had ceased, even regressed. Lastly, no undesirable effect related to nonspecific immunosuppression, tissue toxicity or premature death was observed in the animals treated with $As_2O_5$, indicating its satisfactory tolerance at the therapeutic doses used.

Experiment 6: Demonstration of a potentiating synergistic effect between the arsenic compound $As_2O_5$ and the arsenic compound $As_2O_3$ for treating or preventing autoimmune and lymphoproliferative syndromes in MRL/lpr mice.

Goal: This experiment aims to evaluate the therapeutic efficacy of a combination of the arsenic compound $As_2O_3$ and the compound $As_2O_5$ for topically and/or systemically treating autoimmune and inflammatory tissue damage in MRL/lpr mice.

Methods: MRL/lpr mice (males and females) presenting severe lupus-type skin lesions and cutaneous necrotizing vasculitis were treated 5 times per week, for 8 weeks, by administering an aqueous solution containing either the arsenic compound $As_2O_3$ or the compound $As_2O_5$ or a mixture of both compounds $As_2O_3+As_2O_5$ or phosphate buffer (PBS) as negative control. Weakly effective doses (suboptimal) of $As_2O_3$ or $As_2O_5$ were voluntarily used. The arsenic compounds were administered in aqueous form using compresses or a brush for local treatment or an intraperitoneal injection for systemic treatment.

At the conclusion of the treatment, the blood of each animal was sampled in order to quantify in the serum the levels of autoantibodies (anti-DNA, rheumatoid factor) and cytokines involved in the disease. Skin from the back of each animal was sampled for histological analysis and for analysis of the nature of the inflammatory infiltrate after isolating the cells using enzymatic methods, their counts under the microscope and their analyses by flow cytometry using fluorescent antibodies specific to leukocytes.

Figure 9:
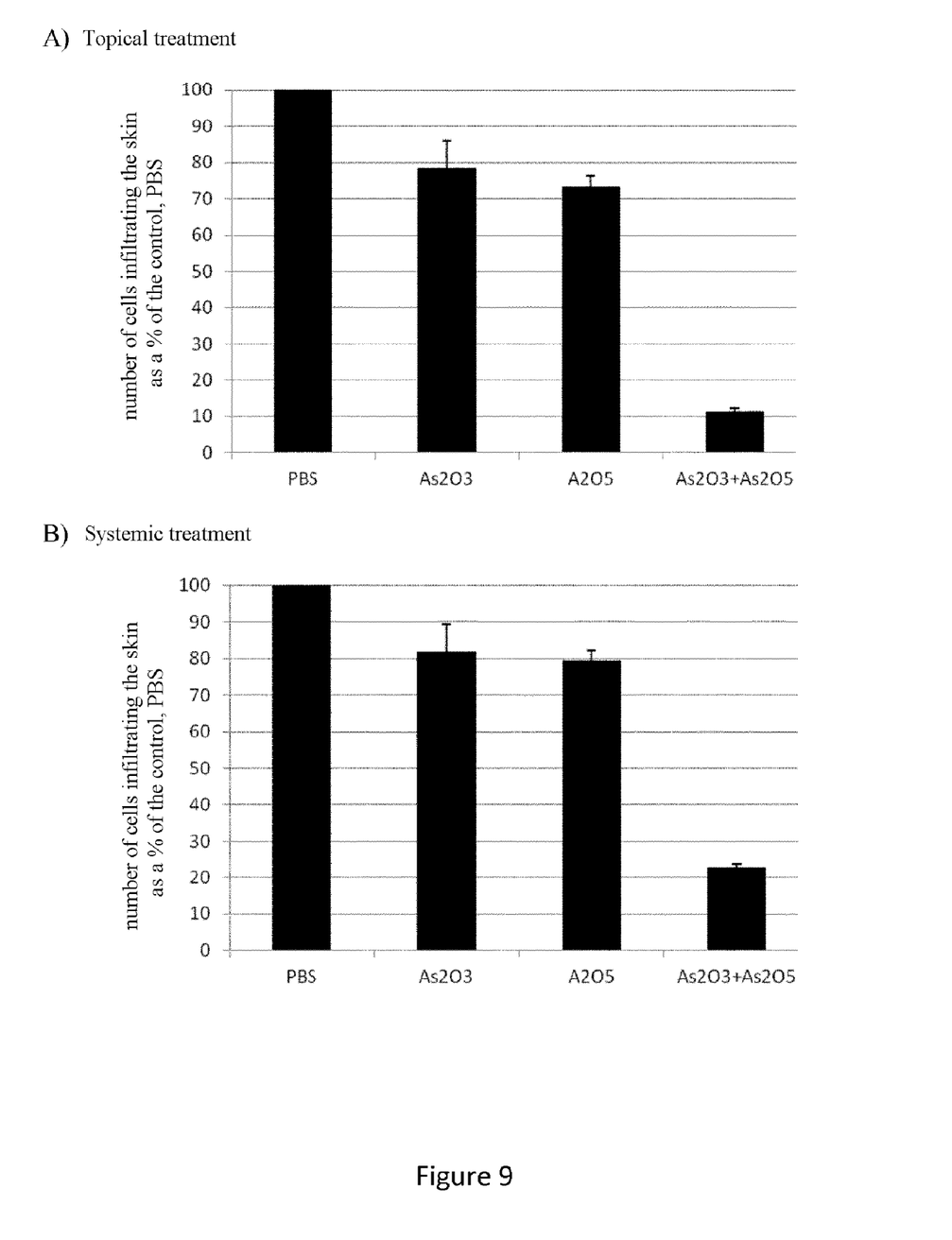
FIG. 9. Quantification of cutaneous inflammatory infiltrate in MRL/lpr mice treated with the arsenic compound $As_2O_5$ or $As_2O_3$ alone or with the combination of both compounds $As_2O_3+As_2O_5$. The number of inflammatory cells infiltrating the skin of MRL/lpr mice (3 females per group) was quantified after 2 months of treatment via local (FIG. 9A) or systemic route (FIG. 9B) with 5 weekly applications of a 0.12 mg/ml solution of $As_2O_3$ or $As_2O_5$ (suboptimal amounts) versus 0.5 mg/ml in FIGS. 1 to 8.
Figure 10:
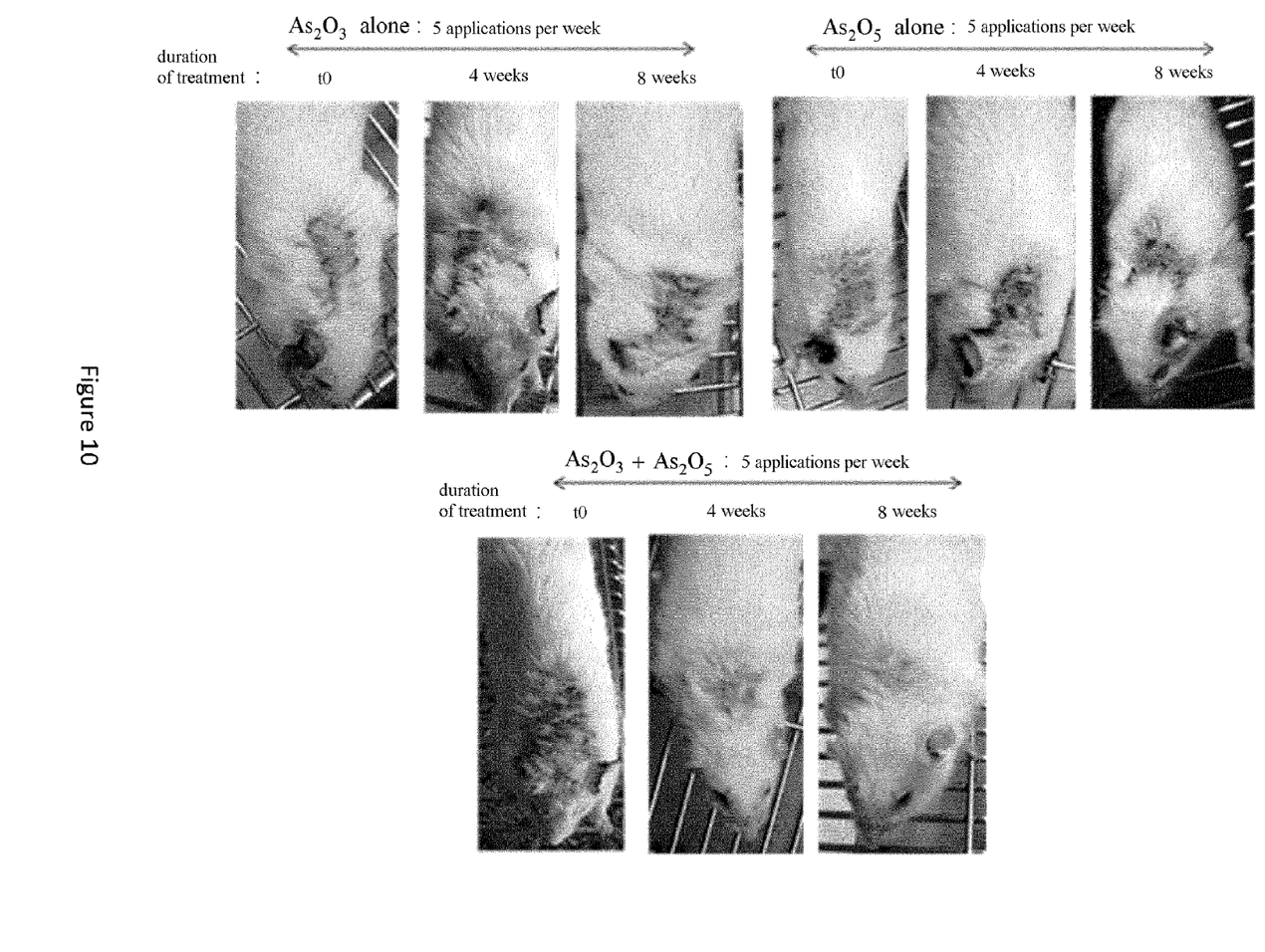
FIG. 10. Local treatment of inflammatory skin damage in MRL/lpr mice with the combination of two compound $As_2O_3+As_2O_5$. Changes in inflammatory skin lesions in female MRL/lpr mice after 0 (t0), 4 and 8 weeks of application of a compress inhibited with a solution containing a suboptimal dose (0.12 mg/ml) of $As_2O_3$ or $As_2O_5$ or with the combination of the two compounds $As_2O_3+As_2O_5$, in 5 applications per week.

Results: FIGS. 9 and 10 show that the therapeutic efficacy of local treatment with a solution containing the compound $As_2O_3$ combined with the compound $As_2O_5$ ($As_2O_3+As_2O_5$) is much higher than that of a solution containing only $As_2O_3$ or $As_2O_5$, whatever the route of injection: local (FIG. 9A) and systemic (FIG. 9B). The 24 MRL/lpr mice used in this experiment presented at the beginning of the treatment (t0) severe skin lesions and vascular lesions of the cutaneous vasculitis type responsible for ear and tail necrosis. Skin from the back of each animal was isolated after 8 weeks of treatment and the cells of the inflammatory infiltrate were isolated and quantified.

The graphs presented in FIGS. 9A and 9B give the number of cells present in the lymphocytic infiltrate in skin lesions from the backs of the mice after treatment with phosphate buffer (PBS), the compound $As_2O_3$, the compound $As_2O_5$ or the combination $As_2O_3+As_2O_5$ (3 mice per group). MRL/lpr mice were voluntarily treated with weakly effective doses (suboptimal) of $As_2O_3$ or $As_2O_5$, as shown by the still high number of cells in the lymphocytic infiltrate at the conclusion of the treatment (FIG. 9) and the presence of severe skin lesions (FIG. 10). On the other hand, when the two arsenic compounds are combined, and at the same doses when administered separately, one observes a nearly complete elimination of the inflammatory infiltrate (FIG. 9), with better efficacy for the topical treatment, and a nearly complete disappearance of the inflammatory tissue lesions, attested by the regrowth of hair (FIG. 10), demonstrating that these two arsenic compounds work synergistically to eliminate the lymphocytic infiltrate.

The invention claimed is:

1. A method for topically treating an autoimmune disease in a human subject, comprising a step of administering topically to the skin of said subject a composition comprising the arsenic compound $As_2O_5$ and a pharmaceutically acceptable carrier or excipient.

2. The method according to claim 1, wherein said administration treats a skin lesion associated with the autoimmune disease.

3. The method according to claim 1, wherein said administration prevents a skin lesion associated with autoimmune disease.

4. The method according to claim 1, wherein said autoimmune diseases is lupus erythematosus.

5. The method according to claim 4, wherein said lupus erythematosus comprises cutaneous lupus erythematosus (CLE).

6. The method according to claim 4, wherein said lupus erythematosus comprises disseminated lupus erythematosus (DLE).

7. The method according to claim 4, wherein said lupus erythematosus comprises systemic lupus erythematosus (SLE).

8. The method according to claim 1, wherein the composition further comprises at least one arsenic compound selected from the list consisting of $As_2O_3$, $As_4O_6$, $As_2S_2$, $As_2S_3$, $As_2S_5$ and $As_4S_4$.

9. The method according to claim 8, wherein the composition further comprises $As_2O_3$.

10. The method according to claim 9, wherein the composition consists of the arsenic compound $As_2O_5$ and the additional arsenic compound $As_2O_3$.

11. The method according to claim 1, wherein the composition comprises between 0.01% and 0.15% of the arsenic compound $As_2O_5$ relative to the total weight of the composition.

12. The method according to claim 11, wherein the composition further comprises between 0.05% and 5% of the arsenic compound $As_2O_3$ relative to the total weight of the composition.

13. The method according to claim 1, wherein the application of $As_2O_5$ is alternated with the administration of at least one additional arsenic compound selected from the list consisting of $As_2O_3$, $As_4O_6$, $As_2S_2$, $As_2S_3$, $As_2S_5$ and $As_4S_4$.

14. The method according to claim 13, wherein the application of $As_2O_5$ is alternated with the administration of the arsenic compound $As_2O_3$.

15. The method according to claim 14, wherein the composition comprises between 0.01% and 0.15% of the arsenic compound $As_2O_5$ relative to the total weight of the composition.

* * * * *